US008474784B2

(12) United States Patent
Kashmirian et al.

(10) Patent No.: US 8,474,784 B2
(45) Date of Patent: Jul. 2, 2013

(54) NON-REOPENING LOCKING PINCH CLAMP FOR TUBING

(75) Inventors: Avtar Singh Kashmirian, Kambah (AU); Joseph J. Dallapiazza, Rochester Hills, MI (US); Craig Douglas Wilson, Bondi Junction (AU); Chris Whelan, Clovelly (AU)

(73) Assignee: Noble House Group Pty. Ltd. (AU)

( * ) Notice: Subject to any disclaimer, the term of this patent is extended or adjusted under 35 U.S.C. 154(b) by 931 days.

(21) Appl. No.: 12/295,885

(22) PCT Filed: Apr. 3, 2007

(86) PCT No.: PCT/AU2007/000430
§ 371 (c)(1),
(2), (4) Date: Dec. 18, 2008

(87) PCT Pub. No.: WO2007/112500
PCT Pub. Date: Oct. 11, 2007

(65) Prior Publication Data
US 2010/0096570 A1    Apr. 22, 2010

(30) Foreign Application Priority Data

Apr. 5, 2006  (AU) ................................. 2006901771
Aug. 25, 2006 (AU) ................................. 2006904608

(51) Int. Cl.
*F16K 7/04* (2006.01)
(52) U.S. Cl.
USPC ............................................ 251/10; 604/250
(58) Field of Classification Search
USPC .................................. 251/10, 4, 9; 604/250
See application file for complete search history.

(56) References Cited

U.S. PATENT DOCUMENTS

| 3,419,245 | A | * | 12/1968 | Scola | 251/10 |
| 3,822,052 | A | * | 7/1974 | Lange | 251/10 |
| 4,053,135 | A | | 10/1977 | Saliaris | |
| 4,235,412 | A | | 11/1980 | Roth | |
| 4,487,205 | A | * | 12/1984 | Di Giovanni et al. | 606/158 |
| 4,589,626 | A | | 5/1986 | Kurtz | |
| 4,643,389 | A | | 2/1987 | Elson | |
| 4,676,476 | A | | 6/1987 | Herrli | |
| 5,203,056 | A | | 4/1993 | Funk | |
| 5,238,218 | A | | 8/1993 | Mackal | |
| 6,592,558 | B2 | | 7/2003 | Quah | |
| D529,374 | S | * | 10/2006 | Watanabe | D8/395 |

(Continued)

FOREIGN PATENT DOCUMENTS

| DE | 10322007 | 7/2004 |
| EP | 0995461 | 9/2004 |
| JP | 2-004384 | 1/1990 |
| WO | WO 03/063945 | 8/2003 |

*Primary Examiner* — John K Fristoe, Jr.
*Assistant Examiner* — R. K. Arundale
(74) *Attorney, Agent, or Firm* — Galbreath Law Offices, P.C.; John A. Galbreath (57) ABSTRACT

A tube clamp having first and second opposed jaws (1012, 1014) joined by a hinge (1016), the jaws (1012, 1014) movable between open and closed positions, the tube clamp adapted to attach to a flexible plastic tube (1024) so that the tube (1024) passes between the jaws (1012, 1014), whereby the flow of fluid through the tube (1024) is permitted when the jaws are open but is blocked when the jaws are brought together to the closed position to pinch closed the tube therebetween, and locking means (1048,1036,1042) to effect substantially permanent and irreversible locking of the jaws (1012, 1014) in the closed position.

23 Claims, 9 Drawing Sheets

U.S. PATENT DOCUMENTS

| | | | |
|---|---|---|---|
| 7,350,761 B1 * | 4/2008 | Stuart | 251/10 |
| 7,686,279 B2 * | 3/2010 | Nerbonne et al. | 251/10 |
| D660,198 S * | 5/2012 | Wanibuchi et al. | D11/220 |
| 2004/0106890 A1 * | 6/2004 | Goudaliez et al. | 604/6.15 |
| 2010/0152681 A1 * | 6/2010 | Mathias | 604/250 |
| 2010/0268161 A1 * | 10/2010 | Traversaz | 604/151 |

* cited by examiner

NON-REOPENING LOCKING PINCH CLAMP FOR TUBING

TECHNICAL FIELD

This invention relates principally to pinch clamps for flexible tubing and, particularly though not exclusively, to one-piece molded-plastic tube clamps for use in medical procedures such as the collection or administration of intravenous (IV) liquids where it is important to permanently lock the clamp so as to securely and permanently close a tube.

However, the present invention may be applied more widely than tube clamps because the means by which permanent locking of a tube clamp can be achieved in accordance with this invention is applicable to other devices, whether for medical use or otherwise.

BACKGROUND

In our prior international patent application PCT/AU99/00918 relating to "Sampling in Blood Collection", we disclosed valve means whereby the first portion of blood collected from a donor could be diverted for sampling before the blood line was connected to the blood collection pouch. An important feature of such valve means is that, once sufficient blood has been diverted for samples, connection to the diversion tube must be permanently closed to be absolutely sure that no contamination from the diversion tube can find its way into the blood collection line to the collection pouch. The valve means disclosed in our prior application was fool-proof in the sense that the collection line could not be opened before the diversion line had been securely closed and that, once closed, the diversion line could not be re-opened or re-connected. This arrangement allowed samples to be drawn off from the diversion line using a sample port and vacuum vial before blood collection commenced.

An important reason for wishing to divert blood for sampling during blood collection is that any skin plug that is cut and retained by the needle can be washed out into the diversion or sample line rather than into the main collection pouch. It is thought that such skin plugs are responsible for much of the bacterial contamination of collected blood pouches.

In an alternative method of 'sampling first', the initial flow of blood is diverted to a sealed sample bag while the blood line to the collection pouch is temporarily blocked, after sufficient sample blood has been collected, the tube to the sample bag is blocked and the tube to the pouch is opened. If desired, samples can be drawn off from the sample bag while blood collection continues. This system is not fool-proof in that manual clamps are used to block the diversion tube and the main blood line. They can be operated in the wrong sequence or the clamp on the diversion line can either be re-opened or not properly closed.

In the collection of blood from donors, or when handling blood or other IV liquids in flexible tubing, one-piece molded-plastic pinch clamps are often used to control fluid flow in the tubes because they are cheap and disposable. In some such situations it is important that the clamps cannot be re-opened after having been finally closed to seal a tube.

The tube clamp with which the present invention is concerned is of the type that comprises a one-piece generally C-shape plastic molding having a pair of opposed jaws joined by a flexible hinge portion and that is adapted to fit onto a flexible plastic tube so that the tube passes between the jaws, whereby the flow of fluid through the tube is permitted when the jaws are open but is blocked when the jaws are brought together to pinch close the tube there-between. This type of tube clamp normally includes releasable locking means that allows the jaws to be clipped together in the closed position.

In blood collection procedures where many donors and blood packs are handled by a single phlebotomist in an hour, it is also important that the clamp be easy to lock closed, that any locking tabs or the like do not protrude so as to be likely to tear or puncture surgical gloves, poke into the user's thumb or fingers or to snag medical dressings, clothing or other fabric. It is also desirable that there is auditory and/or visual confirmation of proper closure. Preferred embodiments of the invention provide a device that satisfies at least some, if not all, of these requirements.

OUTLINE OF THE INVENTION

The present invention involves a non-reopening tube clamp suitable for use on medical tubing, such as the sample diversion tube of a 'sample first' blood collection system. However, the non-reopening clamp can be used with many other situations where the permanent blocking of a flexible intact tube is necessary.

From one aspect, the tube clamp comprises a one-piece generally C-shape plastic molding that is adapted, in its open position, to permit fluid flow through a flexible-walled tube and, in the closed position, to compress and block fluid flow through the tube. The clamp has first and second jaw portions that are spaced apart when the clamp is in its open position and are brought together when the clamp is in its closed position. It has locking means for permanently securing the jaw portions together in the closed position and first and second compressing means adapted to compress the tube between them when the clamp is in the closed position. Apertures are formed in the clamp through which a tube may be threaded so as to guide the tube within the clamp between the first and second compressing means that form part of the respective jaw portions. Preferably, the apertures have closed peripheries so that a tube passed through the apertures cannot be removed except by pulling the tube right through the clamp. After manufacture and assembly, this will generally be prevented by end fittings attached to the tube.

The first and second compressing means are adapted to contact and compress a tube between them when the clamp is in the locked position.

Preferably, the compressing means are substantially linear, thus forming the first and second compressing edges. The edges may be misaligned with one another in the axial direction of the tube so that the tube is subject to both compression and shear when the clamp is in the closed position. This has the advantage that less force is required to close the clamp because the compressing means do not hit head-on but are slightly displaced axially with respect to the axis of the tube.

It is also advantageous to form small teeth on at least one of the compressing edges. The teeth are generally of the same size and spaced periodically. The teeth are usually rounded to prevent puncturing of the tube. If the teeth are formed on both of the compressing edges, the teeth on each edge are spaced to allow locating of the teeth of the first edge in the spaces between the teeth of the second edge when the clamp is in the closed position.

The invention provides for a groove formed in at least one of the compressing edges. The invention provides for rounded or prismoidal grooving.

In one arrangement, one compressing edge is grooved (concave edge) and another is not grooved (convex edge); the concave and convex shapes are adapted such that the concave edge locates the convex edge (with the tube therebetween) when the clamp is in the closed position. The invention provides for different geometries of the concave and the convex edges, including cylindrical and prismoidal. The geometry and dimensions of the concave edge may be different from that of the convex edge. These differences allow for the combined action of the compression and shear forces that arise during the locking action, thus resulting in better blocking of the tube.

The locking means may comprise at least two hook-like tabs that engage a corresponding locking hole or holes on the other. Usually, the outer portion of the locking hole is recessed so that the hook-like tabs on the other portion lies within the recess to thereby inhibit access to the hook when the clamp is in the closed position and is locked by the engagement of the hook-like tab within the locking hole.

Preferably, the locking means comprise first and second hook-like tabs and corresponding first and second holes.

In one arrangement both first and second hook-like tabs are formed on one end of the clamp, whereby the corresponding first and second holes are formed on the other end of the clamp.

In another arrangement the first hook-like tab is formed on one end of the clamp, whereby the second hook-like tab is formed on the other.

Further, the invention provides for Locking means comprising a block and a hook-like tab and two holes: one to accommodate the block and another to accommodate the hook-like tab. In one arrangement both the block and the hook-like tab are on the same end of the clamp. The block has a preferably blunt end to prevent an injury to an operator.

The dimensions of the block and the corresponding hole are adjusted so as to allow the block to snugly fit into the said hole with only a minimal space left between the block and the sides of the hole, thus restricting the movement of the block (and thus the movement of a hook-like tab within the corresponding locking hole) at least in the longitudinal direction (with the clamp being in the locked position) to prevent the clamp from being unintentionally unlocked.

In some arrangements it is preferable to have the transverse dimension of the block larger than the transverse dimension of the hook-like tub.

It is understood in this invention that there may be many variations of the shape and size of the block and the corresponding hole.

From another aspect, the present invention comprises a tube clamp of the type indicated wherein the locking means, when activated, effects substantially permanent and irreversible locking of the jaws in the closed position. Preferably, the locking means comprises a T-shape stud integrally molded with one jaw and a corresponding slot in the other jaw positioned and adapted to accept the stud, the slot being proportioned so that the head of the T-stud can be forced through the slot by folding its sides inwards towards the leg of the T-stud and so that, after passing through the slot, the head of the T-stud is enabled to spring outwards to lock the jaws together. For convenience, it will be said that the T-stud enters the slot from the proximal side and protrudes therefrom on the distal side.

From another aspect, a preferred feature of the above-described locking means is the provision of a recess on the distal side of the slot adapted to accommodate the head of the T-stud so that its distal face does not protrude substantially beyond the distal surface of the jaw in which the slot and recess are formed. A further preferred feature of the locking means is ensuring that the lateral dimension of the recess is somewhat less than the width of the head of the T-stud, when flattened out. In other words, the head of the T-stud will be neatly accommodated by the recess when it is bent or domed so as to be distally convex. Thus, the opening force exerted by the pressure on the closed tube, or by a person's attempt to re-open the clamp, will tend to flatten the head of the T-stud and to jam it lengthwise in the recess so that it will be most difficult to invert and pull through.

We have found that this T-stud design of permanent locking means has the remarkable feature that it is easy to close but very difficult to re-open, unlike most hook and slot locking fasteners where the locking force is commensurate with the unlocking force. By molding the head of the T-stud to be slightly domed, it can be made self-aligning with the slot for even greater ease of entry. Moreover, the slightly domed external (distal) face of the T-stud engaged in the recess presents no protrusion that is likely to snag dressings, puncture surgical gloves or indent the fingers of users. This combination of features allows a phlebotomist to lock many clamps on tubes in a short space of time without tiring or repetitive strain injury.

From another and more general aspect of this invention, the permanent locking means indicated above (i.e., the use of a domed T-stud cooperating with a recessed slot) may be applied to a variety of other devices, especially those for use in the medical field where the properties of ease of closure, smoothness of finish and permanency of closure are important. Examples are patient identification wrist bands and tags, tags for sample or disposal bags, closures for sharps containers and dangerous waste.

DESCRIPTION OF EXAMPLES

Having broadly portrayed the nature of the present invention, ten examples will now be described with reference to the accompanying drawings, in which.

Clamp 210 of the first example shown in FIGS. 1-6 is a unitary plastic injection molding of a flexible and resilient polymeric material such as polypropylene. It is of a generally C-shape and also comprises two opposed relatively stiff jaws 212 and 214, a central relatively flexible hinge portion 216 that joins the jaws together and locking means 218 comprising a first latch portion 220 formed as an extension of jaw 214 and a second latch portion 222 formed in the end of jaw 212. First latch portion 220 comprises a necked tab 226 with shoulders 227, while second latch portion 222 comprises a pair of spaced hooks 223 that are adapted to snap fit around the neck of tab 226 and over shoulders 227 to permanently lock clamp 210 closed (when jaws 212 and 214 are firmly pushed together).

A central aperture 228 is formed in hinge portion 216 and a second aperture 230 of similar size is formed in jaw 212, holes 228 and 230 allowing a flexible tube 232 to be threaded through them so as to be captured by clamp 210.

An inwardly extending abutment 234 is formed on the inner face of jaw 212 and a similar opposing abutment 236 is formed on the inner face of jaw 214, abutment 234 having an inner laterally extending compressing edge 238 and abutment 236 having an opposing lateral extending compressing edge 240. In this example, however, edges 236 and 238 are rounded and cylindrical in shape to better engage and pinch tube 232 between them upon closure of clamp 210.

Figures 1, 4:
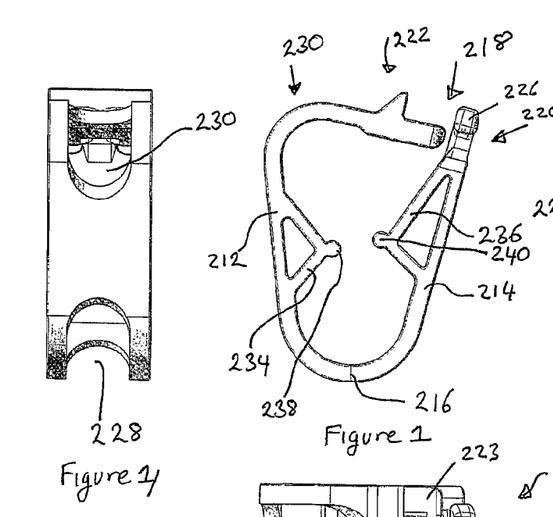
FIG. 1 is a side elevation of the clamp of the first example, shown in the open position.
FIG. 4 is a rear elevation of the clamp of FIG. 1.
Figures 2, 5, 6:
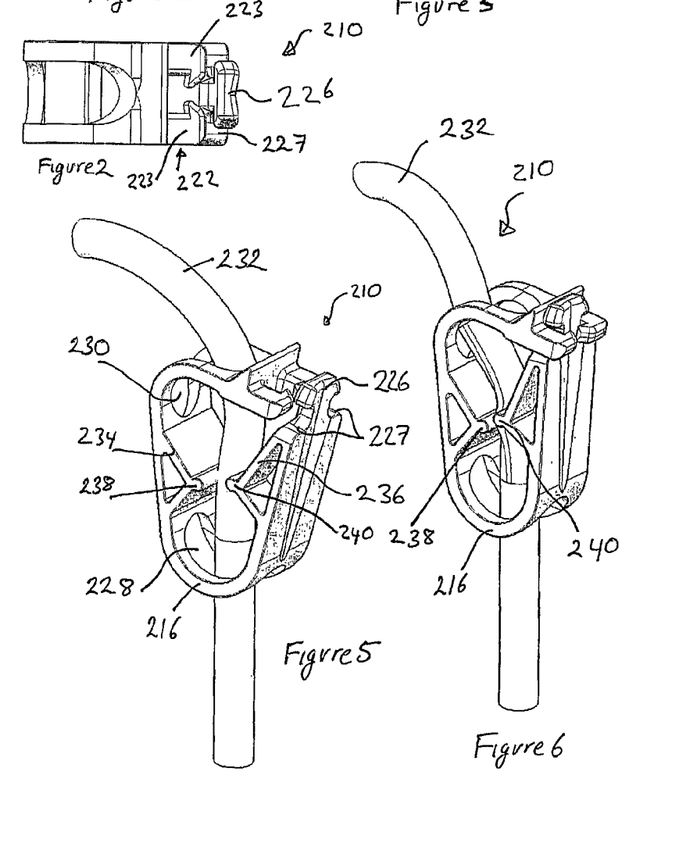
FIG. 2 is a plan view of the clamp of FIG. 1.
FIG. 5 is a perspective view of the clamp of FIG. 1 fitted onto a tube, the clamp being shown in the open position.
FIG. 6 is a perspective view similar to that of FIG. 4 with the clamp of FIG. 1 shown in the closed position.
Figure 3:
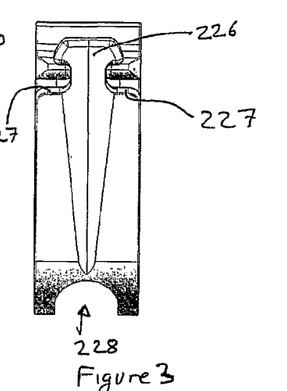
FIG. 3 is a front elevation of the clamp of FIG. 1.

In operation, after tube 232 has been threaded through apertures 228 and 230 of the open clamp so as to lie between compressing edges 238 and 240, as shown in FIG. 5, fluid is free to flow through the tube although tube 232 passes between compressing edges 238 and 240 and is held in that position by apertures 228 and 230. To close clamp 210 and securely cut off fluid flow through tube 232, jaws 212 and 214 are pressed together until latch portions 220 and 220 engage and lock together. This action brings compressing edges 238 and 240 to bear forcibly on tube 232 and to subject the tube to a compressive force so as to be pinched closed.

Figure 7:
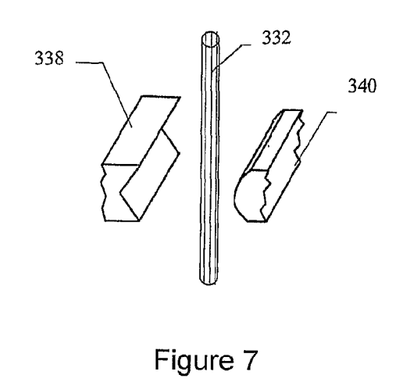
FIG. 7 is a schematic perspective representation of compressing edges according to the second example of the invention.

Compressing edges of the second example are schematically presented in FIG. 7. In this arrangement the first compressing edge 338 is of concave prismoidal shape and is adapted to locate the second convex rounded edge 340 when the clamp is in the closed position, thus blocking a pipe 332 by combined action of compression a shear forces.

Figure 8:
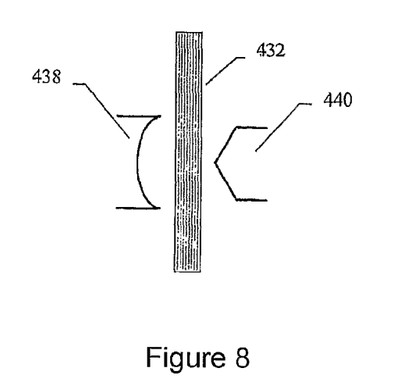
FIG. 8 is a schematic front elevation of compressing edges according to the third example of the invention.

Compressing edges of the third example are schematically presented in FIG. 8. In this arrangement the first compressing edge 438 is of concave rounded shape and is adapted to locate the second convex prismoidal edge 440 when the clamp is in the closed position, thus blocking a pipe 432 by combined action of compressing a shear forces.

Figure 9:
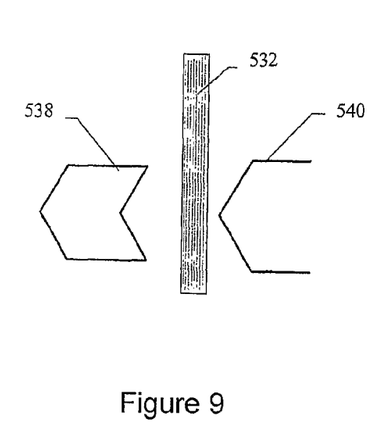
FIG. 9 is a schematic front elevation of compressing edges according to the fourth example of the invention.

Compressing edges of the fourth example are schematically presented in FIG. 9. In this arrangement the first compressing edge 538 is of concave prismoidal shape and is adapted to locate the second convex prismoidal edge 540 when the clamp is in the closed position, thus blocking a pipe 532 by combined action of compressing a shear forces.

Figure 10:
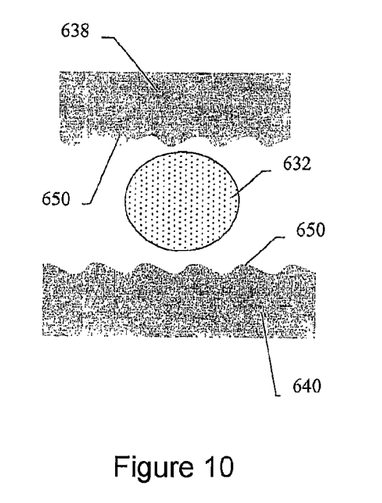
FIG. 10 is a schematic plan view of compressing edges according to the fifth example of the invention.

Compressing means of the fifth example are schematically presented in FIG. 10. In this arrangement small teeth 650 are formed on both first compressing edge 638 and second compressing edge 640. The teeth ensure complete blocking a tube 642 when the clamp is in the closed position.

Figure 11:
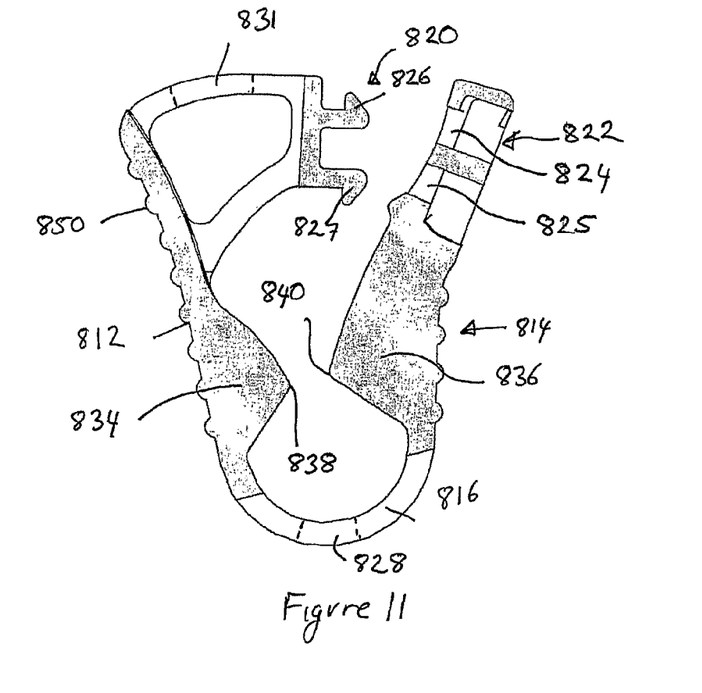
FIG. 11 is a side elevation of the clamp of the sixth example shown in the open position.
Figure 12:
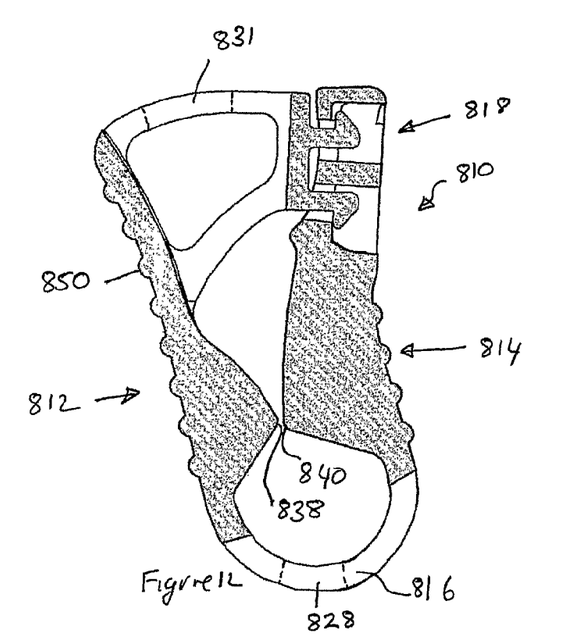
FIG. 12 is a side elevation of the clamp of the sixth example shown in the closed position.

Clamp 810 of the sixth example shown in FIGS. 11-12 is also a unitary plastic injection molding. It comprises two opposed jaws 812 and 814, a central relatively flexible hinge portion 816 that joins the jaws together and locking means 818 comprising a hook portion 820 formed as an extension of jaw 812 and an eye portion 822 formed in the end of jaw 814 and having first hole 824 adapted to snugly accommodate the first barbed end tab 826 of hook portion 820 and second hole 825 adapted to snugly accommodate the second barbed end tab 827 of hook portion 820. A first aperture 828 is formed in hinge portion 816, a second aperture 830 and third aperture 831 of similar size are both formed in hook portion 820, apertures 828, 830 and 831 are allowing a flexible tube (not shown) to be threaded through them so as to be captured by clamp 810. Ribs 850 are formed on external faces of jaws 812 and 814 to ensure good grip with fingers of an operator.

An inwardly extending prismoidal abutment 834 is formed on the inner face of jaw 812 and a similar opposing abutment 836 is formed on the inner face of jaw 814, abutment 834 having an inner compressing edge 838 and abutment 836 having an inner compressing edge 840 that are approximately opposite each other when the clamp is in the open position, as in FIG. 11.

In operation, after tube (not shown) has been threaded through apertures 828, 830 and 831 of the open clamp so as to lie between compressing edges 838 and 840, fluid is free to flow through the tube although the tube passes between compressing edges 838 and 840 and is held in that position by apertures 828, 830 and 831. To close clamp 810 and securely cut off fluid flow through the tube, jaws 812 and 814 are pressed together by applying compression force to their external faces and utilizing ribs 850 until the barbed tabs 826 and 827 of hook portion 720 enter corresponding holes 824 and 825 of eye portion 822 and snap in place. This action brings abutment edges 838 and 840 to bear forcibly on the tube and to subject the tube to a compressive force, thus completely blocking the tube. Implementation of two hooks in this example ensures firm locking of the clamp and makes the closed position practically non-unlockable.

Figure 13:
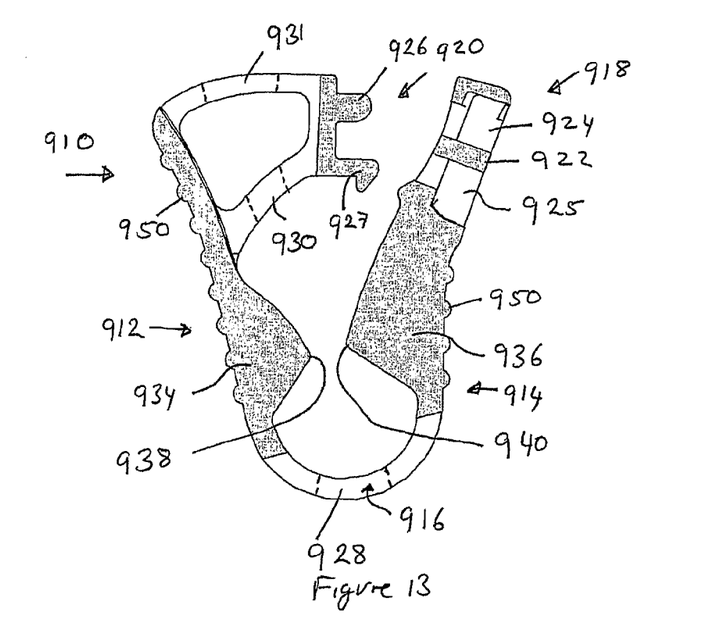
FIG. 13 is a side elevation of the clamp of the seventh example shown in the open position.
Figure 14:
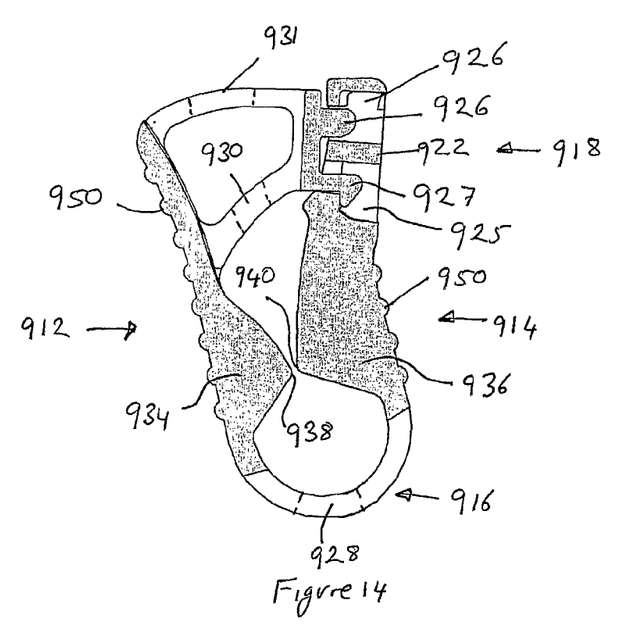
FIG. 14 is a side elevation of the clamp of the seventh example shown in the closed position.

Clamp 910 of the seventh example shown in FIGS. 13-14 is also a unitary plastic injection molding. It comprises two opposed jaws 912 and 914, a central relatively flexible hinge portion 916 that joins the jaws together and locking means 918 comprising a hook portion 920 (in this example comprising a single barbed end tab 927 and a block 926) formed as an extension of jaw 912, and an eye portion 922 formed in the end of jaw 914 and having a guiding hole 924 adapted to accommodate the block 926 of hook portion 920 and a locking hole 925 adapted to snugly accommodate the barbed end tab 927 of hook portion 920. The block 926 is an extension of the hook portion 920 of the jaw 912, the said block having a preferably blunt end that is not limited in shape to that shown in FIGS. 13-14. The guiding hole 924 of the jaw 914 has dimensions sufficient to allow sliding insertion of the block 926 but small enough to prevent or at least significantly restrict the displacement of the said block within the hole 924 in longitudinal direction of the jaw 914, so that the overall distance, in the longitudinal direction of the jaw 914, between the walls of the hole 924 and the block 926 inserted therein is smaller than the overall distance, in longitudinal direction of the jaw 914, between the barbed tab 927 and the walls of the second hole 925 with the said barbed tab inserted therein. A first aperture 928 is formed in hinge portion 916, a second aperture 930 and third aperture 931 of similar size are both formed in hook portion 920, apertures 928, 930 and 931 are allowing a flexible tube (not shown) to be threaded through them so as to be captured by clamp 910. Ribs 950 are formed on external faces of jaws 912 and 914 to ensure good grip with fingers of an operator.

An inwardly extending prismoidal abutment 934 is formed on the inner face of jaw 912 and a similar opposing abutment 936 is formed on the inner face of jaw 914, abutment 934 having an inner compressing edge 938 and abutment 936 having an inner compressing edge 940 that are approximately opposite each other when the clamp is in the open position, as in FIG. 13.

In operation, after tube (not shown) has been threaded through apertures 928, 930 and 931 of the open clamp so as to lie between compressing edges 938 and 940, fluid is free to flow through the tube although the tube passes between compressing edges 938 and 940 and is held in that position by apertures 928, 930 and 931. To close clamp 910 and securely cut off fluid flow through the tube, jaws 912 and 914 are pressed together by applying compression force to their external faces and utilizing ribs 950 until the block 926 and the barbed end tab 927 of hook portion 920 enter corresponding hole 924 and hole 925 of eye portion 922 and the tab 927 snaps in place. This action brings abutment edges 938 and 940 to bear forcibly on the tube and to subject the tube to a compressive force, thus completely blocking the tube. The block 926 restricts relative longitudinal movement of the two jaws, thus preventing disengagement of the hook and, therefore, accidental unlocking of the clamp.

Clamp 1000 of the eighth example shown in FIGS. 15 to 18 is a unitary plastic injection molding of a flexible and resilient polymeric material such as polypropylene or PVC. It is of a generally C-shape and, for the sake of description, can be divided into three portions; namely two opposed relatively stiff jaws 1012 and 1014, a central relatively flexible hinge portion 1016 that joins the jaws together and locking means 1018 comprising a T-stud male element 1020 formed as an extension of jaw 1014 and a female slot element 1022 formed in the end of jaw 1012. A flexible plastic tube 1024 (shown in broken lines) can be threaded longitudinally through clamp 1000 and so that it passes between inwardly-facing wedge-shape abutments 1026 and 1028 that form part of jaws 1012 and 1014 (respectively). Accommodation of tube 1024 is achieved by three longitudinally aligned apertures in clamp 1000, one (1030) in hinge portion 1016 and two (1032 and 1034) in jaw 1014. This method of accommodating tubing in one-piece pinch clamps is well known in the art.

Figure 16:
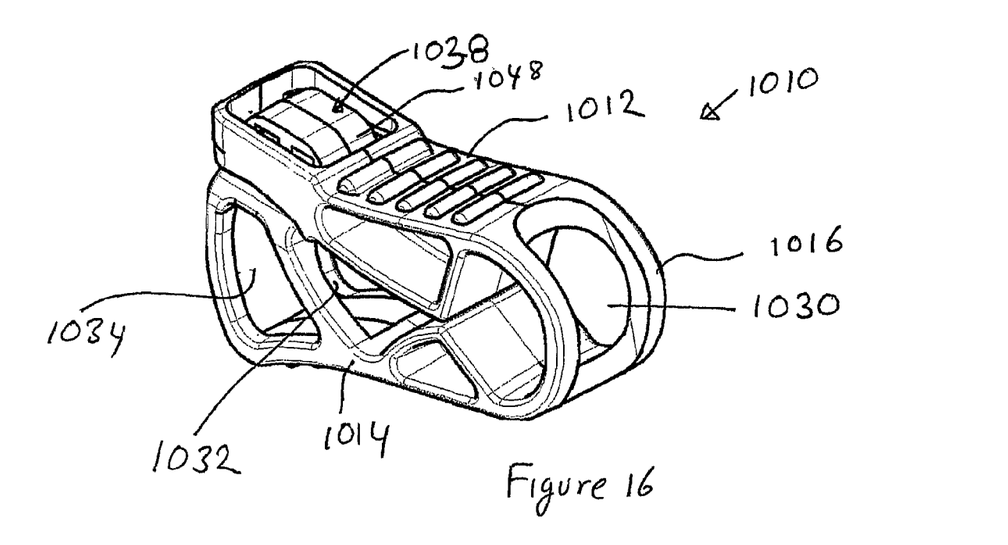
FIG. 16 is a perspective view of the clamp of the eighth example shown in the closed position.
Figure 17A:
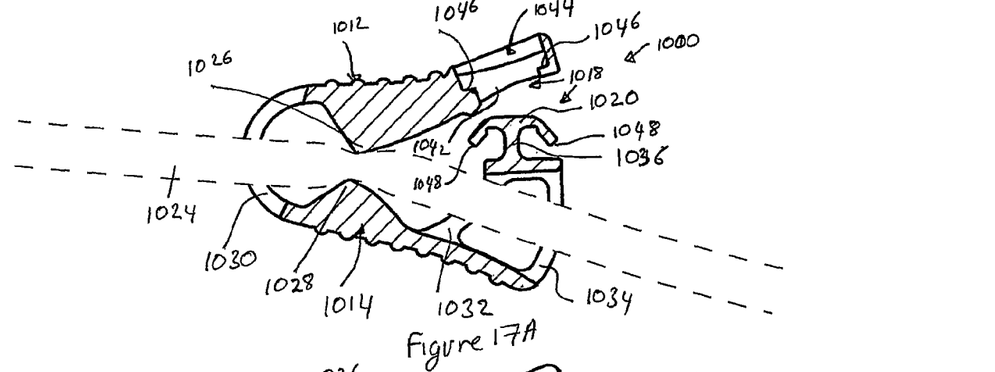
FIGS. 17A and 17B are, respectively, a side elevation and a longitudinal section of the tubing clamp of the eighth example, in the open position.
Figure 17B:
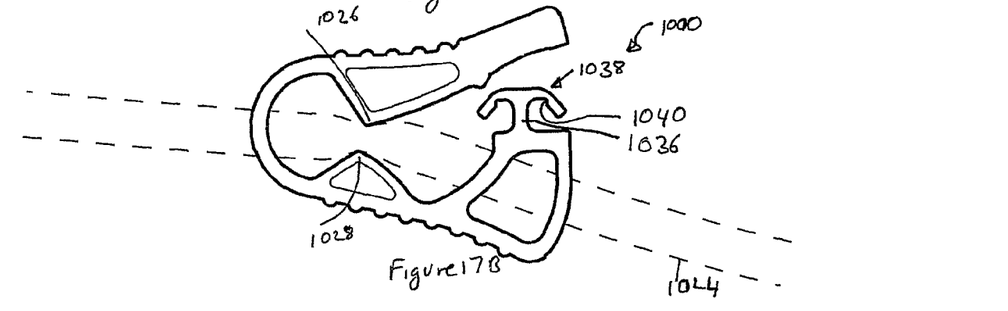

As best seen from FIG. 17A, T-stud element 1020 is molded integrally with the end of jaw 1014 to be up-standing therefrom and to have a leg 1036 that supports a domed head 1038 with significant longitudinal dimension. Head 1038 also has significant lateral dimension, as will also be seen from the external perspective views of FIGS. 15 and 16. The underside of head 1038 is recessed or grooved so as to have areas 1040 of reduced cross-section and greater flexibility.

Figure 15:
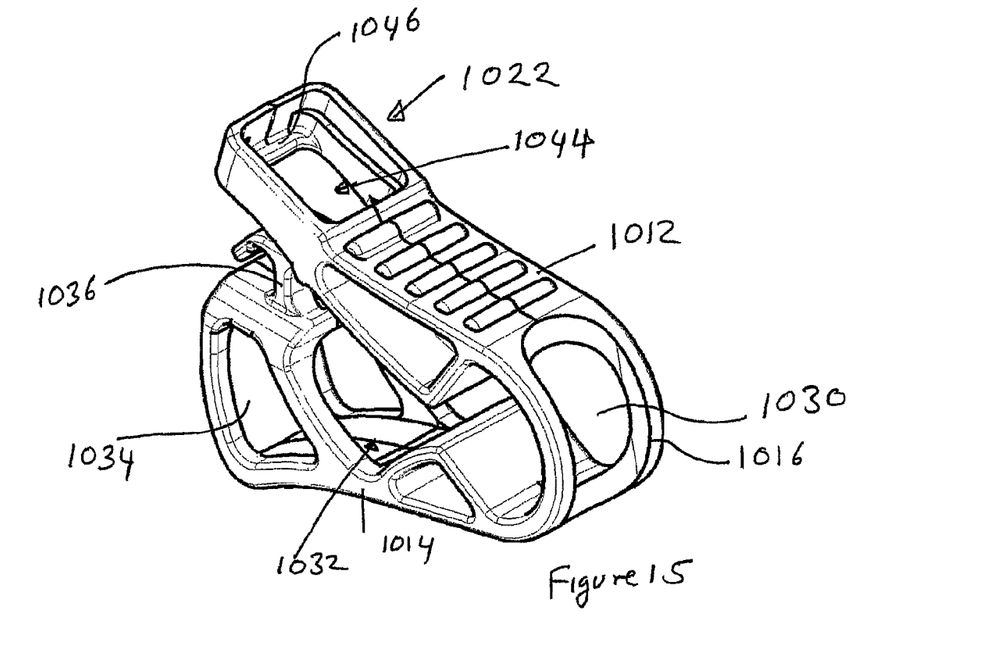
FIG. 15 is a perspective view of the clamp of the eighth example shown in the open position.

It will also be seen from FIGS. 15 and 17A that slot element 1022 comprises a distal entry slot 1042 that opens out into a proximal recess 1044 that is formed so as to provide shoulder abutments 1046 for locating the ends 1048 of T-stud 1020.

Figure 18A:
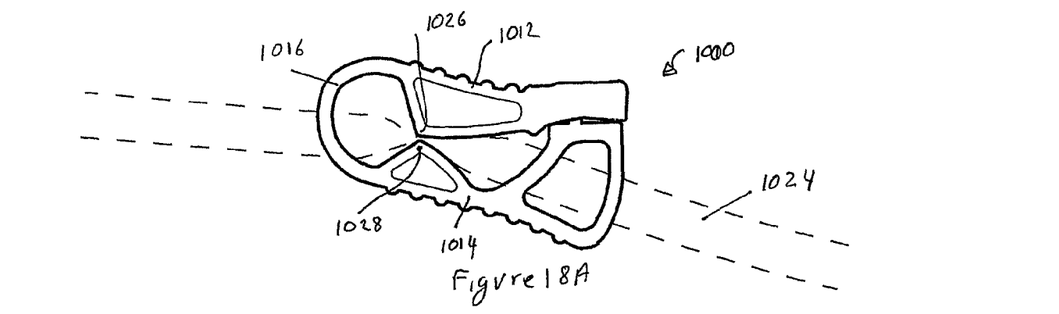
FIGS. 18A and 18B are, respectively, a side elevation and a longitudinal section of the tubing clamp of the eighth example in the closed position.
Figure 18B:
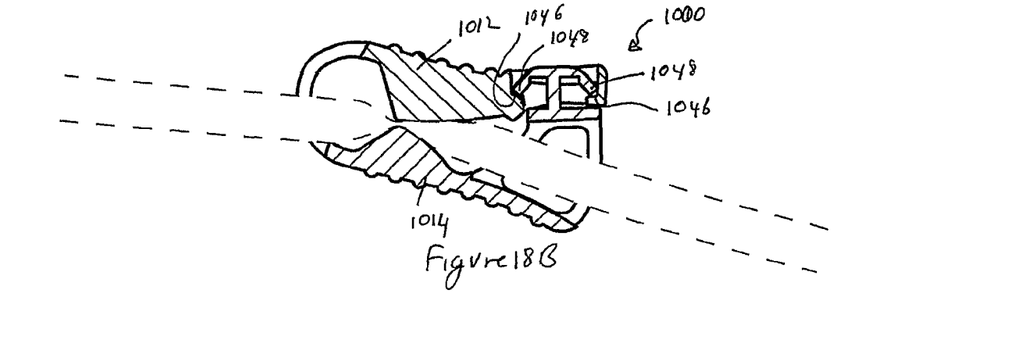

Referring to FIGS. 16, 18A and 18B, which show clamp 1000 in the locked-closed position, it will be seen that head 1038 of T-stud 1020 is substantially entirely housed within recess 1044 of slot element 1022 and the ends 1048 of T-stud 1020 are wedged against shoulders 1046 of the recess, making withdrawal extremely difficult, Indeed, we have found with the design depicted that forcing jaws 1012 and 1014 apart cannot be done by the fingers of a normal person, instead requiring tools and a force of some kilograms that results in snapping leg 1036 rather than the inversion of head 1038.

Figure 19A:
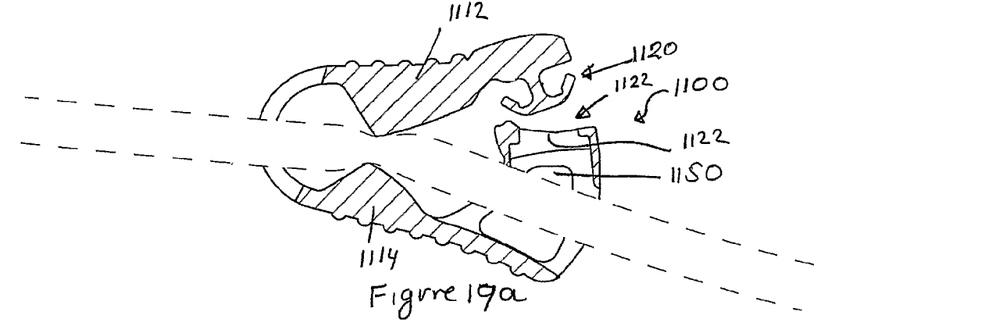
FIGS. 19A and 19B are, respectively, a side elevation and a longitudinal section of the tubing clamp of the ninth example, in the open position.
Figure 19B:
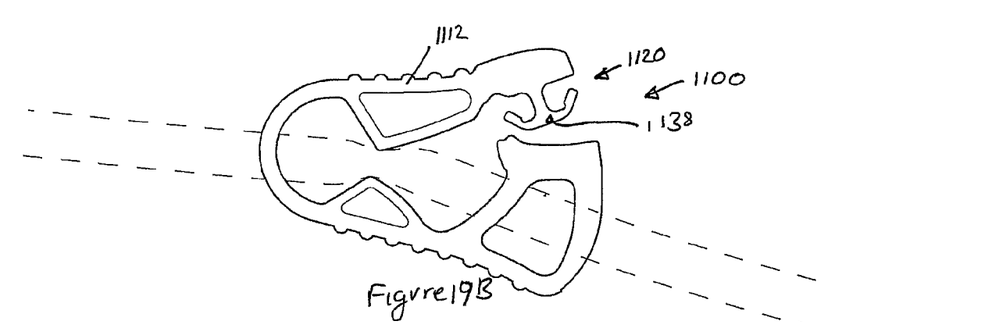
Figure 20A:
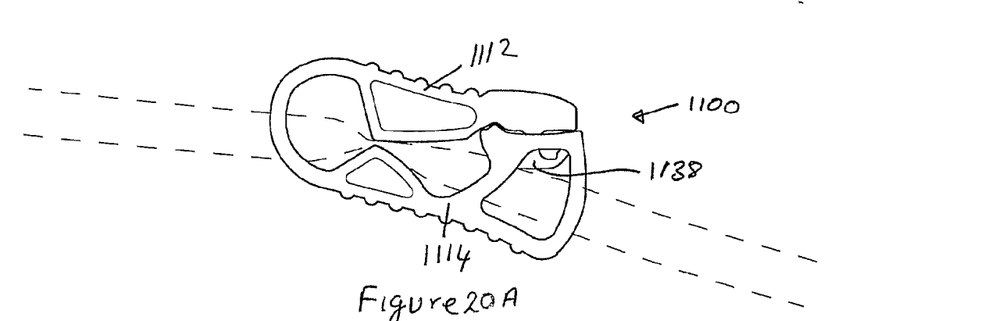
FIGS. 20A and 20B are, respectively, a side elevation and a longitudinal section of the tubing clamp of the ninth example in the closed position.
Figure 20B:
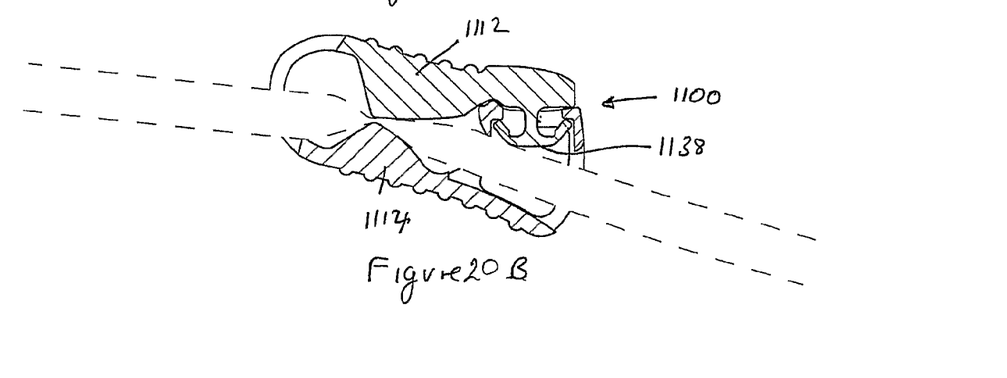

The ninth example, shown in FIGS. 19 to 20, comprises a clamp 1100 that is very similar to clamp 1000 of the eighth example, except that the clamping means has been inverted so that T-stud 1120 now depends from jaw 1112 and recessed slot 1122 is formed in jaw 1114 so that the head 1138 enters the hollow 1150. This arrangement ensures that head 1138 is well out of the way and, indeed, will be very difficult to access if it was intended to use some tool to manipulate the head to open the clamp.

Thus, apart from its inversion, the locking means operates essentially the same way as in the eighth example.

The tenth example of FIGS. 21A to 21D comprises a clamp 1200 that is very similar to clamp 1000 of the eighth example. The tenth example differs from that of the eighth example in that the aperture 1222 is provided with a chamfered surface 1224 on the distal side nearer to the hinge. The recess 1044 still has shoulder abutments 1046 that the ends 1048 overlie and engage when the clamp 1200 is closed.

Figures 21A, 21B:
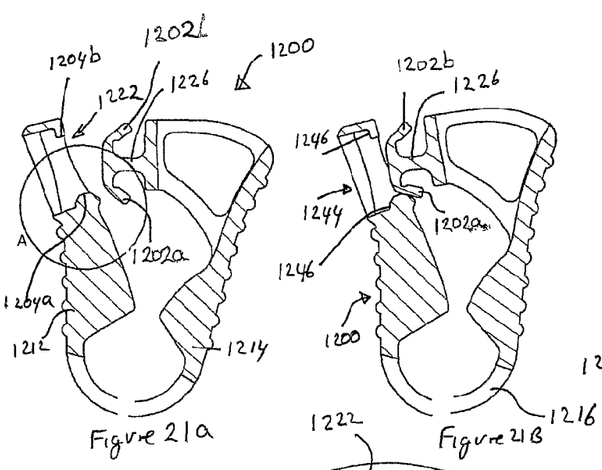
FIGS. 21a to 21c are longitudinal sections of the tubing clamp of the tenth example in an open and two partially closed positions.
Figure 21C:
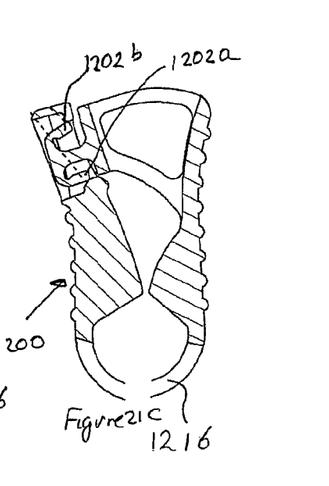
Figure 21D:
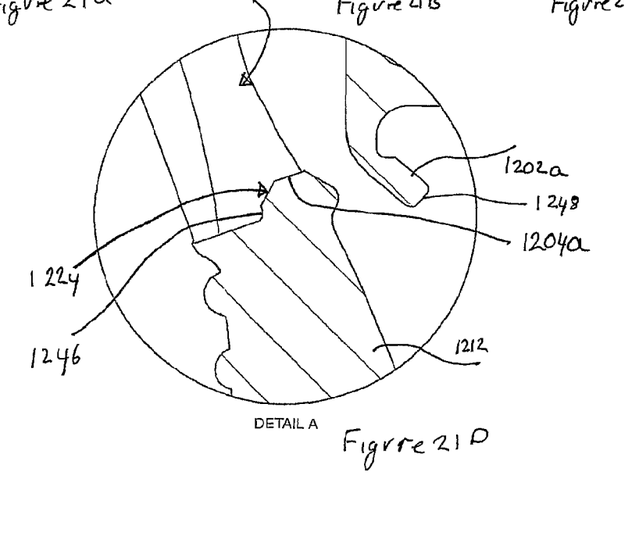
FIG. 21D is a detail view of part of the longitudinal section of the tenth example.

The purpose of the chamfered surface 1224 is to allow the lower leg 1202A to pass though the aperture 1044 and spring outwards substantially at the same time as the upper leg 1202B. This is apparent in FIG. 19C, where the clamp is almost closed and the two legs 1202A & B are still just engaging the sides 1204A & 1204B of the aperture. Further movement results in the lower leg 1202A being able to swing outwards across surface 1224 whilst upper leg 1202B swing outwards across shoulder 1046 substantially simultaneously.

This results in both legs locking at substantially the same time and producing a single audible "click". In the eighth and ninth examples the upper leg clears the aperture before the lower leg and this can result in two separate audible "clicks". If the user does not push hard enough the upper leg releases and produces a click. The user may think the clamp is engaged fully and not continue pushing to engage the lower leg. The tenth example overcomes these disadvantages.

The head of the eighth to tenth examples comprises two arms that extend from the central leg, 1036, 1120 and 1226 respectively in opposite directions to each other. The head may comprise more than two arms, such as three, four or more arms extending radially from the central leg, preferably spaced circumferentially equally from each other.

The head need not be formed of discrete arms. Another alternative is a domed head having a substantially continuous surface. Examples of suitable surfaces include all or part of a cone, a frusto-conical annular flange and part of an ellipsoid.

Clamp 1300 of the eleventh example shown in FIGS. 22 to 25 is similar to the example of FIGS. 15 to 18B and is a unitary plastic injection molding of a flexible and resilient polymeric material such as polypropylene or PVC. It is of a generally C-shape and, for the sake of description, can be divided into three portions; namely two opposed relatively stiff jaws 1312 and 1314, a central relatively flexible hinge portion 1316 that joins the jaws together and locking means 1318 comprising a stud male element 1320 formed as an extension of jaw 1314 and a female slot element 1322 formed in the end of jaw 1312. A flexible plastic tube (not shown) can be threaded longitudinally through clamp 1300 and so that it passes between inwardly-facing wedge-shape abutments 1326 and 1328 that form part of jaws 1312 and 1314 (respectively). Accommodation of tube is achieved by three longitudinally aligned apertures in clamp 1300, one (1330) in hinge portion 1316 and two (1332 and 1334) in jaw 1314.

Figures 22A, 22B, 22C, 22D, 23, 24:
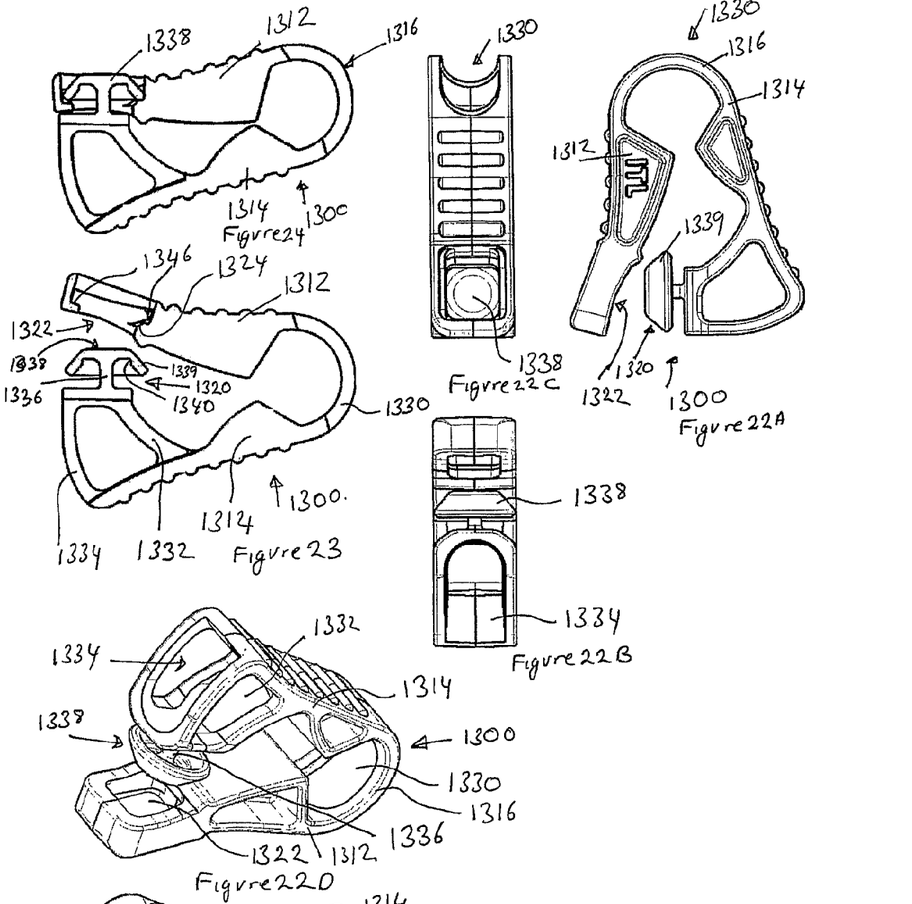
FIGS. 22A to 22D are, respectively, side, plan and rear elevations and a perspective of an eleventh example in an open position.
FIG. 23 is a longitudinal section of the tubing clamp of the tenth example in an open position.
FIG. 24 is a longitudinal section of the tubing clamp of the tenth example in a closed position.

As best seen from FIG. 22A, stud element 1320 is molded integrally with the end of jaw 1314 to be up-standing therefrom and to have a leg 1336 that supports a domed head 1338. The head 1338 is continuous and is in the form of a truncated cone. The underside of head 1338 is recessed or grooved so as to have areas 1340 of reduced cross-section and greater flexibility. This allows the cone shaped wall 1339 to deflect as needed It will also be seen from FIG. 23 that slot element 1322 comprises a distal entry slot 1342 that opens out into a proximal recess 1344 that is formed so as to provide shoulder abutments 1346 for locating the peripheral edge 1348 of wall 1339.

Figure 25:
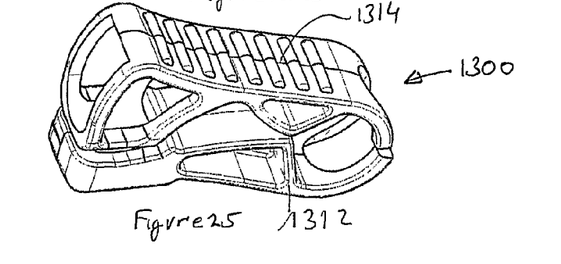
FIG. 25 is a perspective view of the tubing clamp of the tenth example in a closed position.

Referring to FIGS. 24 and 25, which show clamp 1300 in the locked-closed position, it will be seen that head 1338 of stud 1320 is substantially entirely housed within recess 1344 of slot element 1322 and the peripheral edge 1348 of stud 1320 is wedged against shoulders 1346 of the recess, making withdrawal extremely difficult.

To aid insertion, the recess 1322 may have a chamfered surface 1324 as with the example.

Whilst the eleventh example has a generally rectangular slot 1322, the slot 1322 may be made circular to better fit with the head 1338.

Whilst the head 1338 has a continuous wall 1339, if needed one or more slots may be placed in the wall 1339 to provide sufficient flexibility.

While eleven examples have been described and illustrated, it will be appreciated that many changes to the examples can be made without departing from the scope of the present invention as outlined above.

The invention claimed is:

1. A tube clamp having:
   first and second opposed jaws joined by a first hinge,
   the jaws movable between open and closed positions, the tube clamp adapted to attach to a flexible plastic tube so that the tube passes between the jaws, whereby the flow of fluid through the tube is permitted when the jaws are open but is blocked when the jaws are brought together to the closed position to pinch closed the tube therebetween, and
   locking mechanism to effect substantially permanent and irreversible locking of the jaws in the closed position, the locking mechanism comprising:
   a stud on the first jaw comprising a post and a head comprising two arms extending sideways from the post in opposite directions, and
   a corresponding aperture on the second jaw positioned and adapted to accept the stud, the aperture located in a first wall having a proximal side facing the first jaw,
   and being proportioned so that the head of the stud can be forced through the aperture from proximal side by deflecting, bending or folding the two arms inwards towards the post of the stud and so that, after passing through the aperture the two arms spring irreversibly outwards and overlay the distal side of the first wall to lock the jaws together.

2. A tube clamp as claimed in claim 1 including a guard adjacent the aperture on its distal side that prevents or limits access to the head when the clamp is in the closed position.

3. A tube clamp as claimed in claim 1 wherein the distal side of the aperture is surrounded or substantially surrounded by an upstanding second wall.

4. A tube clamp as claimed in claim 3 wherein, in the closed position, the two arms engage the second wall.

5. A tube clamp as claimed in claim 1 wherein the aperture is located in a base of a recess on the distal side of the second jaw.

6. A tube clamp as claimed in claim 5, wherein the recess has a side wall or walls, and wherein in the closed position, the two arms engage the side wall or walls of the recess.

7. A tube clamp as claimed in claim 5 wherein the recess has a size less than the maximum size of the head.

8. A tube clamp as claimed in claim 5 wherein if, in the closed position, the jaws are moved apart the two arms engage the side wall or walls of the recess.

9. A tube clamp as claimed in claim 1 wherein the two arms are configured to deflect, bend or fold outwards if, in the closed position, the jaws are moved apart.

10. A tube clamp as claimed claim 1 wherein each arm has a first section that extends generally perpendicular to the post and a second section, depending from the first section, which extends outwards and towards the first jaw.

11. A tube clamp as claimed in claim 10 wherein the junction of the first and second sections comprises a resilient second hinge.

12. A tube clamp as claimed in claim 11 wherein a first arm extends towards the first hinge and a second arm extends away from the first hinge.

13. A tube clamp as claimed in claim 1 wherein the two arms engage the aperture and the distal side of the first wall is configured so that the two arms pass through the aperture and spring outwards substantially simultaneously.

14. A tube clamp as claimed in claim 1 wherein at least part of the distal side of the first wall is chamfered to present a surface extending at an angle to the aperture.

15. A tube clamp as claimed in claim 1 wherein the distal side of the first wall nearest to the first hinge is chamfered to present a surface extending at an angle to the aperture.

16. A tube clamp having:
   first and second opposed jaws joined by a hinge,
   the jaws movable between open and closed positions, the tube clamp adapted to attach to a flexible plastic tube so that the tube passes between the jaws, whereby the flow of fluid through the tube is permitted when the laws are open but is blocked when the jaws are brought together to the closed position to pinch closed the tube therebetween, and
   a locking mechanism to effect substantially permanent and irreversible locking of the jaws in the closed position, the locking mechanism comprising:
   a first leg extending from one of the jaws and a second leg extending from one of the jaws, the legs extending generally parallel to each other, at least one of the legs having a barb, and
   at least one corresponding aperture on the other of the laws positioned and adapted to accept the legs, the at least one aperture being proportioned so that passage of the barb or barbs through the respective aperture occurs by deflecting, bending or folding at least a portion of the respective leg sideways and so that, after at least the barb or barbs has passed through the aperture, the leg or legs spring irreversibly sideways to position the barbs over the surface of the jaw defining the respective aperture to lock the laws together, and wherein one of the legs has a barb extending generally sideways to the leg and the other leg does not have a barb.

17. A tube clamp as claimed in claim 16 wherein both legs extend from the same jaw.

18. A tube clamp as claimed in claim 16 wherein a separate aperture is provided for each leg.

19. A tube clamp as claimed in claim 16 wherein the leg without a barb is a snug fit in the corresponding aperture.

20. A tube clamp as claimed in claim 16 including a guard adjacent the at least one aperture on its distal side that prevents or limits access to the barb or barbs when the clamp is in the closed position.

21. A tube clamp as claimed in claim 16 wherein the distal side of the least one aperture is surrounded or substantially surrounded by an upstanding second wall.

22. A tube clamp as claimed in claim 16 wherein, in the closed position, at least part of the periphery of the head engages the second wall.

23. A tube clamp as claimed in claim 16 wherein the at least one aperture is located in a base of a corresponding recess on the distal side of the second jaw.

\* \* \* \* \*